United States Patent
Boggs

(10) Patent No.: US 10,760,700 B2
(45) Date of Patent: Sep. 1, 2020

(54) OXYGEN FLOW REMOTE-CONTROL ASSEMBLY

(71) Applicant: Larry Boggs, South Park, PA (US)

(72) Inventor: Larry Boggs, South Park, PA (US)

( * ) Notice: Subject to any disclaimer, the term of this patent is extended or adjusted under 35 U.S.C. 154(b) by 69 days.

(21) Appl. No.: 16/150,828

(22) Filed: Oct. 3, 2018

(65) Prior Publication Data

US 2020/0109793 A1   Apr. 9, 2020

(51) Int. Cl.
*F16K 31/04*   (2006.01)
*C01B 13/02*   (2006.01)
*G05D 7/06*   (2006.01)
*F16K 31/05*   (2006.01)
*A61M 16/00*   (2006.01)

(52) U.S. Cl.
CPC ............ *F16K 31/041* (2013.01); *C01B 13/02* (2013.01); *F16K 31/04* (2013.01); *F16K 31/043* (2013.01); *F16K 31/046* (2013.01); *F16K 31/047* (2013.01); *F16K 31/05* (2013.01); *F16K 31/055* (2013.01); *G05D 7/0635* (2013.01); *A61M 16/024* (2017.08); *Y10T 137/7065* (2015.04)

(58) Field of Classification Search
CPC .............. A61M 16/024; A61M 16/101; A61M 2205/103; A61M 2205/106; A61M 2205/502; A61M 2205/8206; A61M 2209/01; F16K 31/04; F16K 31/043; F16K 31/046; F16K 31/05; F16K 31/055; Y10T 137/7065; G06F 19/3418
USPC ..... 251/129.03, 129.04, 291–293; 137/382.5
See application file for complete search history.

(56) References Cited

U.S. PATENT DOCUMENTS

| | | | |
|---|---|---|---|
| 5,440,477 A * | 8/1995 | Rohrberg | F17C 13/02 137/588 |
| 5,603,315 A | 2/1997 | Sasso | |
| 5,755,224 A * | 5/1998 | Good | A62B 9/02 128/204.18 |
| 5,794,645 A * | 8/1998 | Rohrberg | F17C 13/003 137/1 |
| 6,283,139 B1 * | 9/2001 | Symonds | A01G 25/165 137/78.3 |
| 6,328,053 B1 * | 12/2001 | Slaydon | F16K 1/30 137/15.17 |
| 6,470,885 B1 | 10/2002 | Blue | |
| 6,595,487 B2 * | 7/2003 | Johansen | F16K 31/04 251/129.04 |
| 7,552,731 B2 | 6/2009 | Jorczak | |
| 7,641,172 B2 * | 1/2010 | Richards | E03B 7/071 251/129.04 |
| 7,900,650 B1 * | 3/2011 | Wilson | F17D 5/00 137/551 |
| 8,677,998 B2 * | 3/2014 | Yamaura | A61M 16/10 128/204.21 |

(Continued)

Primary Examiner — Matthew W Jellett

(57) ABSTRACT

A remote-control assembly for adjusting a flow of oxygen from an oxygen concentrator includes an inducer module and remote controller. The inducer module, which comprises a receiver, is selectively couplable to the oxygen concentrator so that the inducer module is operationally coupled to a flow rate control knob of the oxygen concentrator. The remote controller comprises a transmitter and is positioned to selectively and wirelessly communicate a command to the inducer module, via the receiver, positioning the inducer module to turn the flow rate control knob to adjust a flow of oxygen from the oxygen concentrator.

9 Claims, 4 Drawing Sheets

(56) References Cited

U.S. PATENT DOCUMENTS

| | | | |
|---|---|---|---|
| 9,550,031 B2* | 1/2017 | Van Sickle | A61M 15/00 |
| 2005/0103341 A1* | 5/2005 | Deane | B01D 53/053 |
| | | | 128/204.26 |
| 2007/0227360 A1* | 10/2007 | Atlas | A61M 16/10 |
| | | | 96/121 |
| 2010/0078017 A1 | 4/2010 | Andrieus | |
| 2014/0196788 A1* | 7/2014 | Taft | F17C 13/04 |
| | | | 137/1 |

* cited by examiner

OXYGEN FLOW REMOTE-CONTROL ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relate to remote-control assemblies and more particularly pertains to a new remote-control assembly for adjusting a flow of oxygen from an oxygen concentrator.

BRIEF SUMMARY OF THE INVENTION

An embodiment of the disclosure meets the needs presented above by generally comprising an inducer module and remote controller. The inducer module, which comprises a receiver, is selectively couplable to an oxygen concentrator so that the inducer module is operationally coupled to a flow rate control knob of the oxygen concentrator. The remote controller comprises a transmitter and is positioned to selectively and wirelessly communicate a command to the inducer module, via the receiver, positioning the inducer module to turn the flow rate control knob to adjust a flow of oxygen from the oxygen concentrator.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
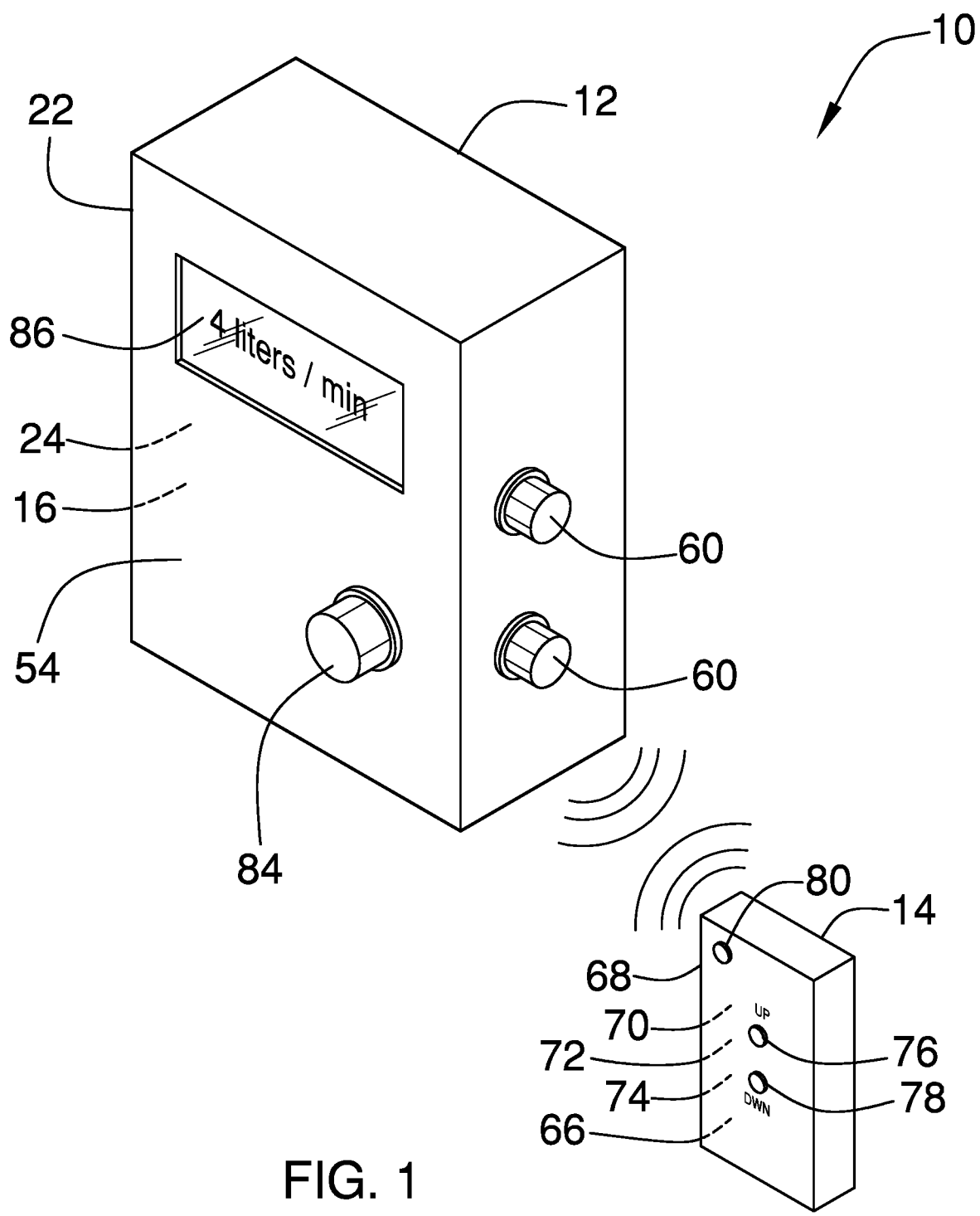
FIG. 1 is an isometric perspective view of a remote-control assembly according to an embodiment of the disclosure.

With reference now to the drawings, and in particular to FIGS. 1 through 5 thereof, a new remote-control assembly embodying the principles and concepts of an embodiment of the disclosure and generally designated by the reference numeral 10 will be described.

As best illustrated in FIGS. 1 through 5, the remote-control assembly 10 generally comprises an inducer module 12 and remote controller 14. The inducer module 12, which comprises a receiver 16, is selectively couplable to an oxygen concentrator 18 so that the inducer module 12 is operationally coupled to a flow rate control knob 20 of the oxygen concentrator 18. In one embodiment, as shown in FIG. 1, the receiver 16 is radio-frequency type.

The inducer module 12 comprises a first housing 22 that defines an interior space 24. An orifice 26 is positioned in a back 28 of the first housing 22. The orifice 26 is configured to insert the flow rate control knob 20 into the interior space 24.

Figure 5:
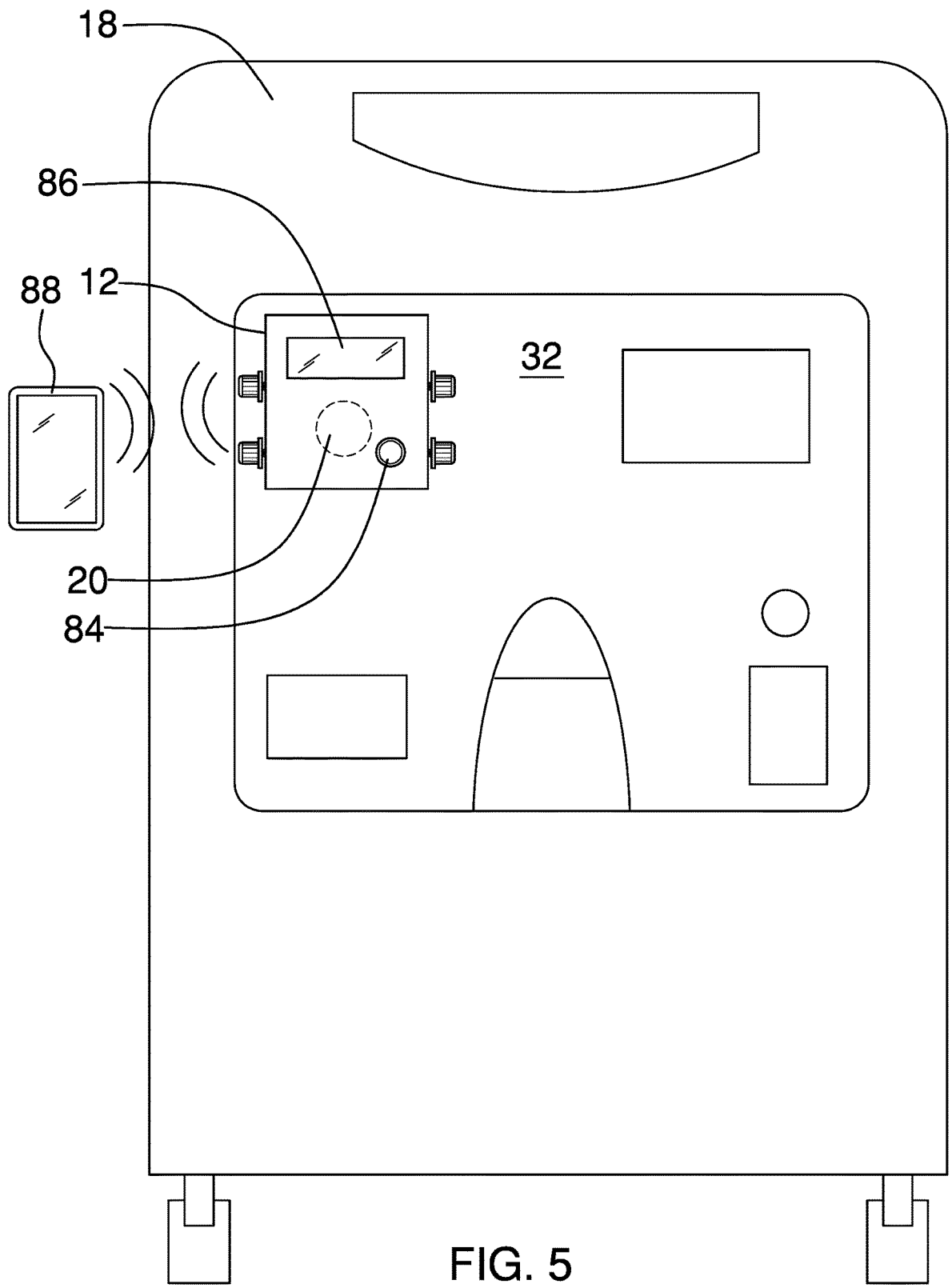
FIG. 5 is an in-use view of an embodiment of the disclosure.

A coupler 30 is coupled to the back 28 of the first housing 22. The coupler 30 is configured to couple the first housing 22 to a surface 32 of the oxygen concentrator 18 with the flow rate control knob 20 positioned through the orifice 26, as shown in FIG. 5. The coupler 30 comprises adhesive 34.

The receiver 16, a first battery 36, a first microprocessor 38, and a plurality of actuators 40 are coupled to the first housing 22 and are positioned in the interior space 24. The first microprocessor 38 is operationally coupled to the first battery 36, the receiver 16 and the plurality of actuators 40. Each actuator 40 is operationally coupled to the flow rate control knob 20. The plurality of actuators 40 comprises four actuators 40.

Figure 3:
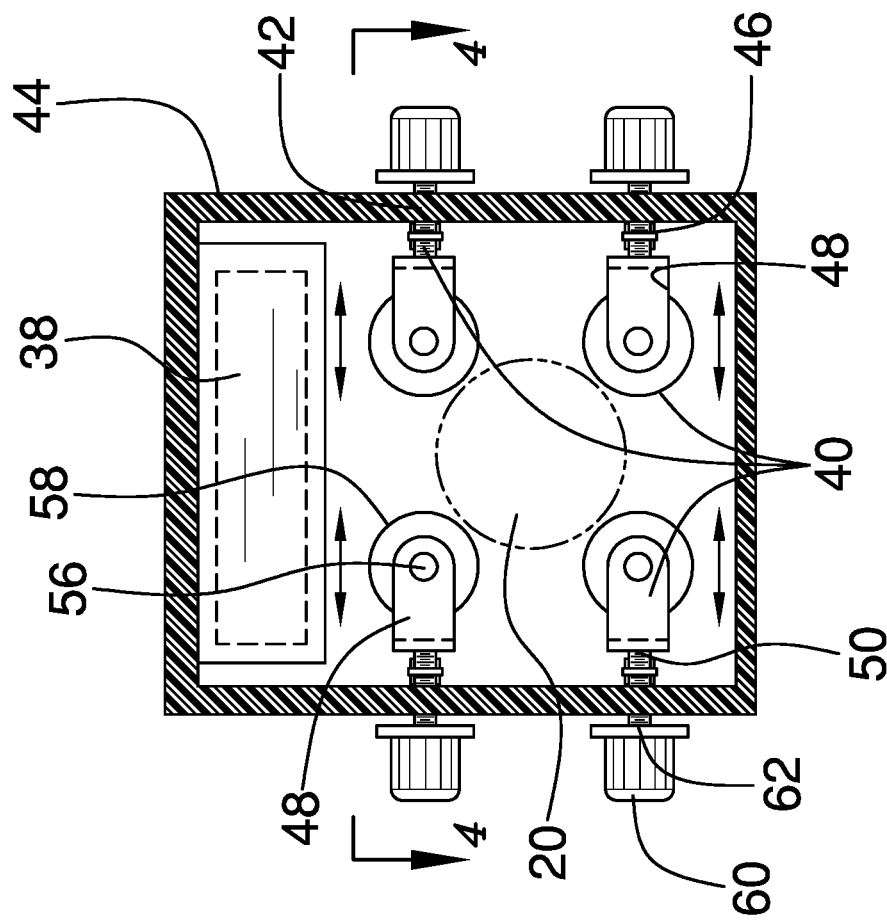
FIG. 3 is a cross-sectional view of an embodiment of the disclosure.
Figure 2:
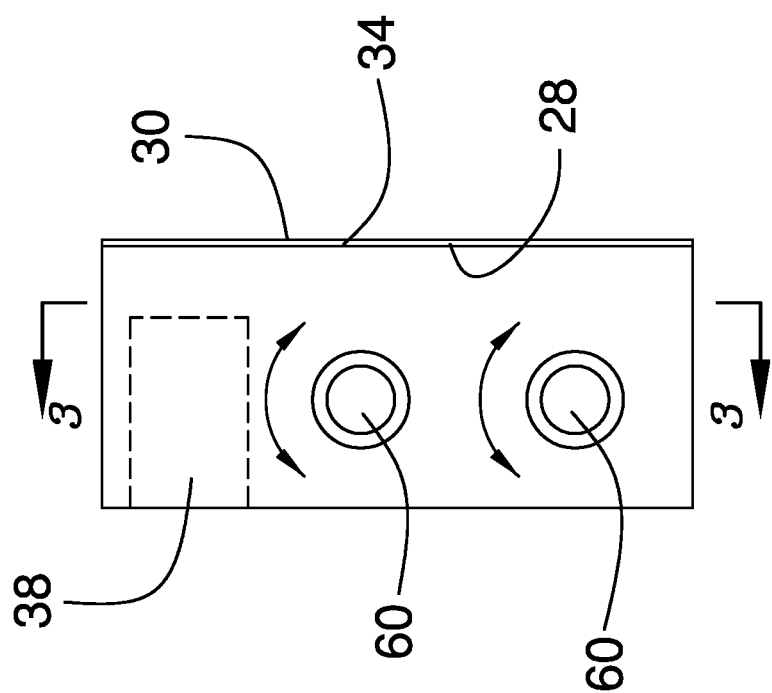
FIG. 2 is a side view of an embodiment of the disclosure.
Figure 4:
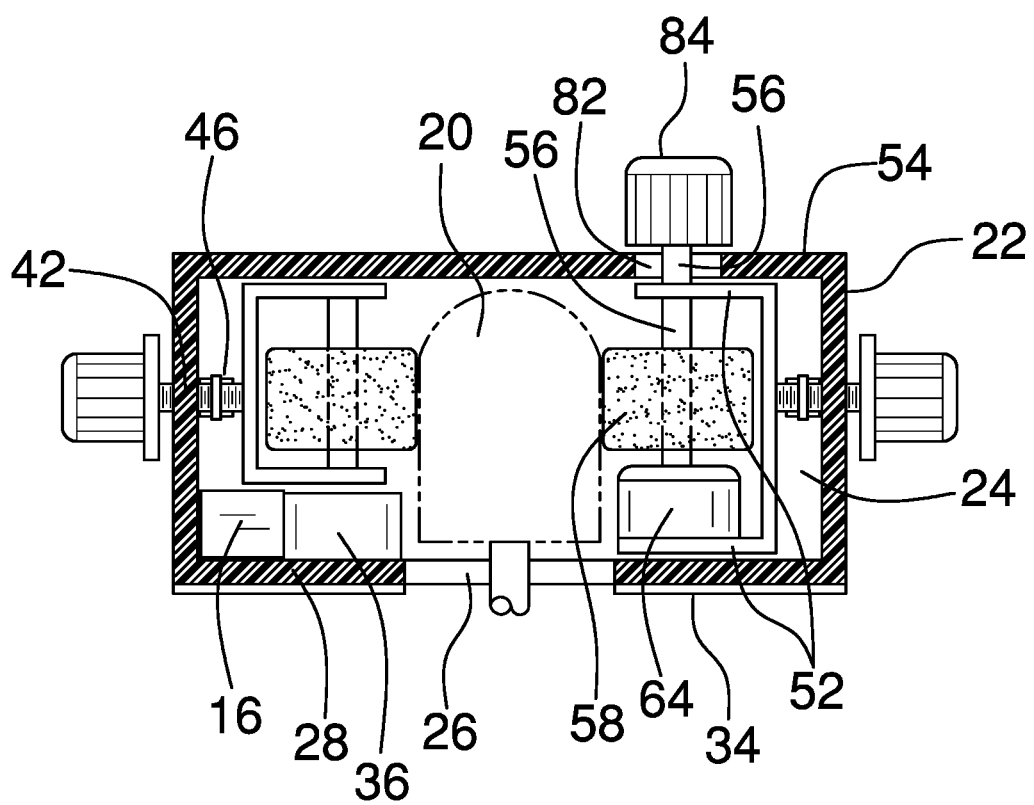
FIG. 4 is a cross-sectional view of an embodiment of the disclosure.

Each actuator 40 comprises a hole 42 that is threaded and positioned in a respective side 44 of the first housing 22, as shown in FIGS. 3 and 4. A thumbscrew 46 is threadedly positioned through the hole 42. A bracket 48, which is C-channel type, is rotationally coupled to a first terminus 50 of the thumbscrew 46. Opposing ends 52 of the bracket 48 are positioned singly proximate to the back 28 and a front 54 of the first housing 22. An axle 56 is rotationally coupled to and extends between the opposing ends 52 of the bracket 48. A wheel 58, which is resiliently compressible, is coupled to the axle 56. A screw knob 60 that is coupled to a second terminus 62 of the thumbscrew 46 is configured to be grasped in digits of a hand of a user and selectively rotated to urge the bracket 48 toward the flow rate control knob 20 so that the wheel 58 frictionally couples to the flow rate control knob 20. The ability to selectively adjust the actuators 40 allows the assembly 10 to be user with oxygen concentrators 18 having a variety of sizes of flow rate control knobs 20.

A motor 64 is coupled to the bracket 48. The motor 64 is operationally coupled to the axle 56. The motor 64 is positioned to selectively rotate the wheel 58 concurrently with the axle 56 so that the wheel 58 rotates the flow rate control knob 20.

The remote controller 14 comprises a transmitter 66 and is positioned to selectively and wirelessly communicate a command to the inducer module 12, via the receiver 16, positioning the inducer module 12 to turn the flow rate control knob 20 to adjust a flow of oxygen from the oxygen concentrator 18. The remote controller 14 allows a user to selectively adjust the flow of oxygen when positioned distally from the oxygen concentrator 18.

The remote controller 14 comprises a second housing 68 that defines an internal space 70, as shown in FIG. 1. The transmitter 66, a second battery 72 and a second microprocessor 74 are coupled to the second housing 68 and are positioned in the internal space 70. The second microprocessor 74 is operationally coupled to the second battery 72 and the transmitter 66.

A first button 76 is coupled to the second housing 68. The first button 76, which is depressible, is operationally coupled to the second microprocessor 74. The first button 76 is configured to be depressed to signal the second microprocessor 74 to command the transmitter 66 to transmit an increase command to the inducer module 12, via the receiver 16, positioning the inducer module 12 to turn the flow rate control knob 20 to increase the flow of the oxygen from the oxygen concentrator 18.

A second button 78 is coupled to the second housing 68. The second button 78, which is depressible, is operationally coupled to the second microprocessor 74. The second button 78 is configured to be depressed to signal the second microprocessor 74 to command the transmitter 66 to transmit a decrease command to the inducer module 12, via the receiver 16, positioning the inducer module 12 to turn the flow rate control knob 20 to decrease the flow of the oxygen from the oxygen concentrator 18.

A third button 80 is coupled to the second housing 68. The third button 80, which is depressible, is operationally coupled to the second battery 72 and the second microprocessor 74. The third button 80 is configured to be depressed a first time to operationally couple the second microprocessor 74 to the second battery 72 and to be depressed a second time to decouple the second microprocessor 74 from the second battery 72.

A slot 82 is positioned in the front 54 of the first housing 22. A respective axle 56 extends through the slot 82. An adjustment knob 84 is coupled to the respective axle 56 so that the adjustment knob 84 is positioned externally to the first housing 22. The adjustment knob 84 is configured to be grasped in the digits of the hand of the user to selectively turn the respective axle 56 to manually turn the flow rate control knob 20 to adjust the flow of oxygen from the oxygen concentrator 18.

A display 86 is coupled to the front 54 of the first housing 22, as shown in FIG. 1. The display 86 is operationally coupled to the first microprocessor 38. The first microprocessor 38 is positioned to command the display 86 to present the flow rate of the oxygen from the oxygen concentrator 18.

In another embodiment, as shown in FIG. 5, programming code 88 is positioned on an electronic device of the user that enables the user to send the command to the inducer module 12, via the receiver 16, positioning the inducer module 12 to turn the flow rate control knob 20 to adjust the flow of the oxygen from the oxygen concentrator 18.

In use, the first housing 22 is adhesively coupled to the surface 32 of the oxygen concentrator 18 with the flow rate control knob 20 positioned through the orifice 26. The thumbscrews 46 are used to adjust the brackets 48 so that the wheels 58 are frictionally coupled to the flow rate control knob 20. As needed, the remote controller 14 is used to send the command to the inducer module 12 to adjust the flow of the oxygen from the oxygen concentrator 18.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be only one of the elements.

I claim:

1. A remote-control assembly comprising:
    an inducer module couplable to an oxygen concentrator such that the inducer module is operationally coupled to a flow rate control knob of the oxygen concentrator, the inducer module comprising a receiver;
    a remote controller comprising a transmitter wherein the transmitter is positioned for selectively wirelessly communicating a command to the inducer module via the receiver positioning the inducer module for turning the flow rate control knob for adjusting a flow of oxygen from the oxygen concentrator;
    the inducer module comprising
        a first housing defining an interior space, the receiver being coupled to the first housing and positioned in the interior space,
        an orifice positioned in a back of the first housing wherein the orifice is configured for inserting the flow rate control knob into the interior space,
        a coupler coupled to the back of the first housing wherein the coupler is configured for coupling the first housing to a surface of the oxygen concentrator with the flow rate control knob positioned through the orifice,
        a first battery coupled to the first housing and positioned in the interior space, a first microprocessor coupled to the first housing and positioned in the interior space, the first microprocessor being operationally coupled to the first battery and the receiver, and a plurality of actuators coupled to the first housing and positioned in the interior space, the plurality of actuators being operationally coupled to the first microprocessor, each actuator being operationally coupled to the flow rate control knob; and each actuator comprising a hole positioned in a respective side of the first housing, the hole being threaded, a thumbscrew threadedly positioned through the hole, a bracket rotationally coupled to a first terminus of the thumbscrew, the bracket being C-channel type such that opposing ends of the bracket are positioned singly proximate to the back and a front of the first housing, an axle rotationally coupled to and extending between the opposing ends of the bracket, a wheel coupled to the axle, the wheel being resiliently compressible wherein a screw knob coupled to a second terminus of the thumbscrew is configured for grasping in digits of a hand of a user for being selectively rotated for urging the bracket toward the flow rate control knob such that the wheel frictionally couples to the flow rate control knob, and a motor coupled to the bracket, the motor being operationally coupled to the axle wherein the motor is positioned for selectively rotating the wheel concurrently with the axle such that the wheel rotates the flow rate control knob.

2. The assembly of claim 1, further including the receiver being radio-frequency type.

3. The assembly of claim 1, further including the coupler comprising adhesive.

4. The assembly of claim 1, further including the plurality of actuators comprising four actuators.

5. The assembly of claim 1, further including the remote controller comprising:

a second housing defining an internal space, the transmitter being coupled to the second housing and positioned in the internal space;

a second battery coupled to the second housing and positioned in the internal space;

a second microprocessor coupled to the second housing and positioned in the internal space, the second microprocessor being operationally coupled to the second battery and the transmitter;

a first button coupled to the second housing, the first button being depressible, the first button being operationally coupled to the second microprocessor wherein the first button is configured for depressing for signaling the second microprocessor for commanding the transmitter for transmitting an increase command to the inducer module via the receiver positioning the inducer module for turning the flow rate control knob for increasing the flow of the oxygen from the oxygen concentrator;

a second button coupled to the second housing, the second button being depressible, the second button being operationally coupled to the second microprocessor wherein the second button is configured for depressing for signaling the second microprocessor for commanding the transmitter for transmitting a decrease command to the inducer module via the receiver positioning the inducer module for turning the flow rate control knob for decreasing the flow of the oxygen from the oxygen concentrator; and a third button coupled to the second housing, the third button being depressible, the third button being operationally coupled to the second battery and the second microprocessor wherein the third button is configured for depressing a first time for operationally coupling the second microprocessor to the second battery and for depressing a second time for decoupling the second microprocessor from the second battery.

6. The assembly of claim 1, further comprising:

a slot positioned in the front of the first housing, a respective axle extending through the slot; and an adjustment knob coupled to the respective axle such that the adjustment knob is positioned externally to the first housing wherein the adjustment knob is configured for grasping in the digits of the hand of the user for selectively turning the respective axle for manually turning the flow rate control knob for adjusting the flow of the oxygen from the oxygen concentrator.

7. The assembly of claim 1, further including a display coupled to a front of the first housing, the display being operationally coupled to the first microprocessor wherein the first microprocessor is positioned for commanding the display for presenting the flow rate of the oxygen from the oxygen concentrator.

8. The assembly of claim 1, further including programming code positioned to be executed on an electronic device of a user enabling the user for sending the command to the inducer module via the receiver positioning the inducer module for turning the flow rate control knob for adjusting the flow of the oxygen from the oxygen concentrator.

9. A remote-control assembly comprising:

an inducer module couplable to an oxygen concentrator such that the inducer module is operationally coupled to a flow rate control knob of the oxygen concentrator, the inducer module comprising a receiver, the receiver being radio-frequency type, the inducer module comprising:

a first housing defining an interior space, the receiver being coupled to the first housing and positioned in the interior space, an orifice positioned in a back of the first housing wherein the orifice is configured for inserting the flow rate control knob into the interior space, a coupler coupled to the back of the first housing wherein the coupler is configured for coupling the first housing to a surface of the oxygen concentrator with the flow rate control knob positioned through the orifice, the coupler comprising adhesive, a first battery coupled to the first housing and positioned in the interior space, a first microprocessor coupled to the first housing and positioned in the interior space, the first microprocessor being operationally coupled to the first battery and the receiver, a plurality of actuators coupled to the first housing and positioned in the interior space, the plurality of actuators being operationally coupled to the first microprocessor, each actuator being operationally coupled to the flow rate control knob, the plurality of actuators comprising four actuators, each actuator comprising:

a hole positioned in a respective side of the first housing, the hole being threaded, a thumbscrew threadedly positioned through the hole, a bracket rotationally coupled to a first terminus of the thumbscrew, the bracket being C-channel type such that opposing ends of the bracket are positioned singly proximate to the back and a front of the first housing, an axle rotationally coupled to and extending between the opposing ends of the bracket, a wheel coupled to the axle, the wheel being resiliently compressible wherein a screw knob coupled to a second terminus of the thumbscrew is configured for grasping in digits of a hand of a user for being selectively rotated for urging the bracket toward the flow rate control knob such that the wheel frictionally couples to the flow rate control knob, and a motor coupled to the bracket, the motor being operationally coupled to the axle wherein the motor is positioned for selectively rotating the wheel concurrently with the axle such that the wheel rotates the flow rate control knob;

a remote controller comprising a transmitter wherein the transmitter is positioned for selectively wirelessly communicating a command to the inducer module via the receiver positioning the inducer module for turning the flow rate control knob for adjusting a flow of oxygen from the oxygen concentrator, the remote controller comprising:

a second housing defining an internal space, the transmitter being coupled to the second housing and positioned in the internal space, a second battery coupled to the second housing and positioned in the internal space, a second microprocessor coupled to the second housing and positioned in the internal space, the second microprocessor being operationally coupled to the second battery and the transmitter, a first button coupled to the second housing, the first button being depressible, the first button being operationally coupled to the second microprocessor wherein the first button is configured for depressing for signaling the second microprocessor for commanding the transmitter for transmitting an increase command to the inducer module via the receiver positioning the inducer module for turning the flow rate control knob for increasing the flow of the oxygen from the oxygen concentrator, a second button coupled to the second housing, the second button being depressible, the second button being operationally coupled to the second microprocessor wherein the second button is configured for depressing for signaling the second microprocessor for commanding the transmitter for transmitting a decrease command to the inducer module via the receiver positioning the inducer module for turning the flow rate control knob for decreasing the flow of the oxygen from the oxygen concentrator, and a third button coupled to the second housing, the third button being depressible, the third button being operationally coupled to the second battery and the second microprocessor wherein the third button is configured for depressing a first time for operationally coupling the second microprocessor to the second battery and for depressing a second time for decoupling the second microprocessor from the second battery;

a slot positioned in the front of the first housing, a respective axle extending through the slot;

an adjustment knob coupled to the respective axle such that the adjustment knob is positioned externally to the first housing wherein the adjustment knob is configured for grasping in the digits of the hand of the user for selectively turning the respective axle for manually turning the flow rate control knob for adjusting the flow of the oxygen from the oxygen concentrator;

a display coupled to the front of the first housing, the display being operationally coupled to the first microprocessor wherein the first microprocessor is positioned for commanding the display for presenting the flow rate of the oxygen from the oxygen concentrator; and programming code positioned to be executed on an electronic device of the user enabling the user for sending the command to the inducer module via the receiver positioning the inducer module for turning the flow rate control knob for adjusting the flow of the oxygen from the oxygen concentrator.

\* \* \* \* \*